(12) United States Patent
Thommen et al.

(10) Patent No.: US 11,951,021 B2
(45) Date of Patent: Apr. 9, 2024

(54) SURGICAL IMPLANT POSITION DETECTION

(71) Applicant: DePuy Synthes Products, Inc., Raynham, MA (US)

(72) Inventors: Daniel Thommen, Oberdorf Basel Landschaft (CH); Eric Buehlmann, Duxbury, MA (US); Marc Puls, Thorigen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 7 days.

(21) Appl. No.: 17/538,395

(22) Filed: Nov. 30, 2021

(65) Prior Publication Data
US 2023/0165606 A1 Jun. 1, 2023

(51) Int. Cl.
*A61F 2/46* (2006.01)
*A61F 2/44* (2006.01)
*A61B 17/00* (2006.01)
*A61B 17/70* (2006.01)
(Continued)

(52) U.S. Cl.
CPC .......... *A61F 2/4611* (2013.01); *A61F 2/4455* (2013.01); *A61F 2/4465* (2013.01); *A61B 2017/00022* (2013.01); *A61B 17/7053* (2013.01); *A61B 17/7091* (2013.01);
(Continued)

(58) Field of Classification Search
CPC .... A61F 2/4611; A61F 2/4465; A61F 2/4455; A61F 2/446; A61F 2/447; A61F 2002/30538
See application file for complete search history.

(56) References Cited

U.S. PATENT DOCUMENTS

2003/0135275 A1* 7/2003 Garcia ............... A61B 17/1671
623/17.11
2006/0229627 A1* 10/2006 Hunt ..................... A61F 2/4465
606/86 R
(Continued)

FOREIGN PATENT DOCUMENTS

WO 2010/121030 A2 10/2010
WO 2014/140445 A1 9/2014
(Continued)

*Primary Examiner* — Julianna N Harvey
*Assistant Examiner* — Anna V. Little
(74) *Attorney, Agent, or Firm* — Condo Roccia Koptiw LLP

(57) ABSTRACT

Systems, methods, and devices are disclosed for surgical systems comprising an applicator having a first shaft, an implant having a first member pivotably and detachably coupled to the first shaft, and a second member for converting rotational motion of the implant to a translational offset, and at least one of a sensor for determining the offset or an indicator for indicating the offset, provided that the indicator is not a protrusion located at an end of the applicator. A controller may be provided, the controller being configured to receive offset data from the sensor, determine an angle of the implant in a patient using dimensions of the implant and the offset, and display a current position of the implant relative to patient anatomy. The applicator may have a second shaft slidably disposed on the first shaft along an axis defined by a longitudinal axis of the applicator.

12 Claims, 8 Drawing Sheets

(51) Int. Cl.
*A61B 34/10* (2016.01)
*A61B 90/00* (2016.01)

(52) U.S. Cl.
CPC ......... *A61B 34/10* (2016.02); *A61B 2034/102* (2016.02); *A61B 90/39* (2016.02)

(56) References Cited

U.S. PATENT DOCUMENTS

| | | | | |
|---|---|---|---|---|
| 2006/0235426 | A1* | 10/2006 | Lim | A61F 2/4465 606/99 |
| 2007/0225726 | A1* | 9/2007 | Dye | A61F 2/4465 606/99 |
| 2008/0009880 | A1* | 1/2008 | Warnick | A61F 2/4455 623/17.16 |
| 2008/0077153 | A1* | 3/2008 | Pernsteiner | A61F 2/4611 606/99 |
| 2008/0077241 | A1* | 3/2008 | Nguyen | A61F 2/4684 606/85 |
| 2008/0109005 | A1* | 5/2008 | Trudeau | A61F 2/4611 623/17.16 |
| 2008/0119935 | A1* | 5/2008 | Alvarez | A61F 2/4611 606/151 |
| 2008/0140085 | A1* | 6/2008 | Gately | A61F 2/4611 606/205 |
| 2009/0234364 | A1* | 9/2009 | Crook | A61F 2/4465 606/99 |
| 2010/0191337 | A1* | 7/2010 | Zamani | A61F 2/4465 623/17.16 |
| 2011/0106259 | A1* | 5/2011 | Lindenmann | A61F 2/4684 623/17.16 |
| 2012/0083885 | A1* | 4/2012 | Thibodeau | A61F 2/4465 623/17.16 |
| 2014/0172105 | A1 | 6/2014 | Frasier et al. | |
| 2016/0045333 | A1* | 2/2016 | Baynham | A61F 2/446 623/17.16 |
| 2017/0172759 | A1* | 6/2017 | Kukkar | A61F 2/4465 |
| 2018/0256363 | A1* | 9/2018 | Moon | A61F 2/30771 |
| 2018/0289506 | A1* | 10/2018 | Kim | A61F 2/4465 |
| 2018/0303624 | A1* | 10/2018 | Shoshtaev | A61F 2/4465 |
| 2019/0038434 | A1* | 2/2019 | Saito | A61F 2/4611 |
| 2020/0297513 | A1 | 9/2020 | Zellmer et al. | |

FOREIGN PATENT DOCUMENTS

| | | | | |
|---|---|---|---|---|
| WO | WO-2014140445 A1 * | 9/2014 | ......... | A61F 2/4465 |
| WO | 2017/059375 A1 | 4/2017 | | |

* cited by examiner

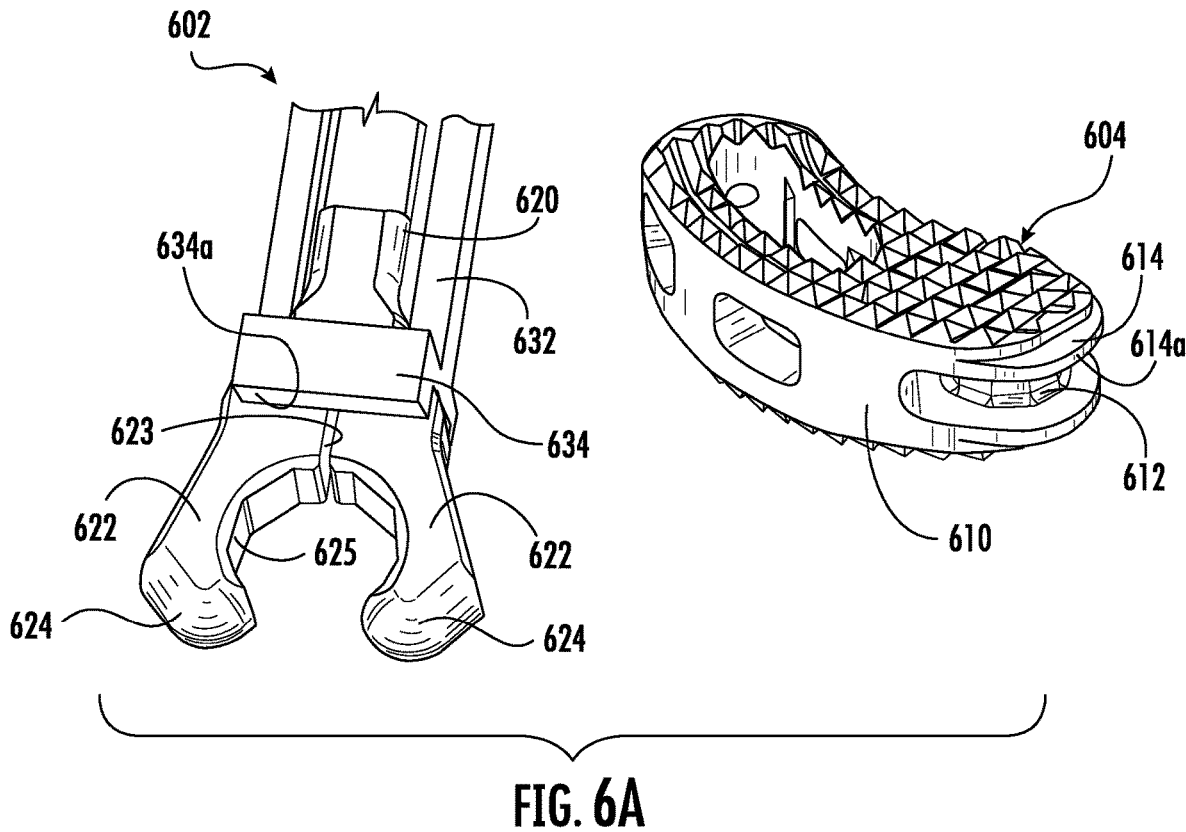
FIG. 6A
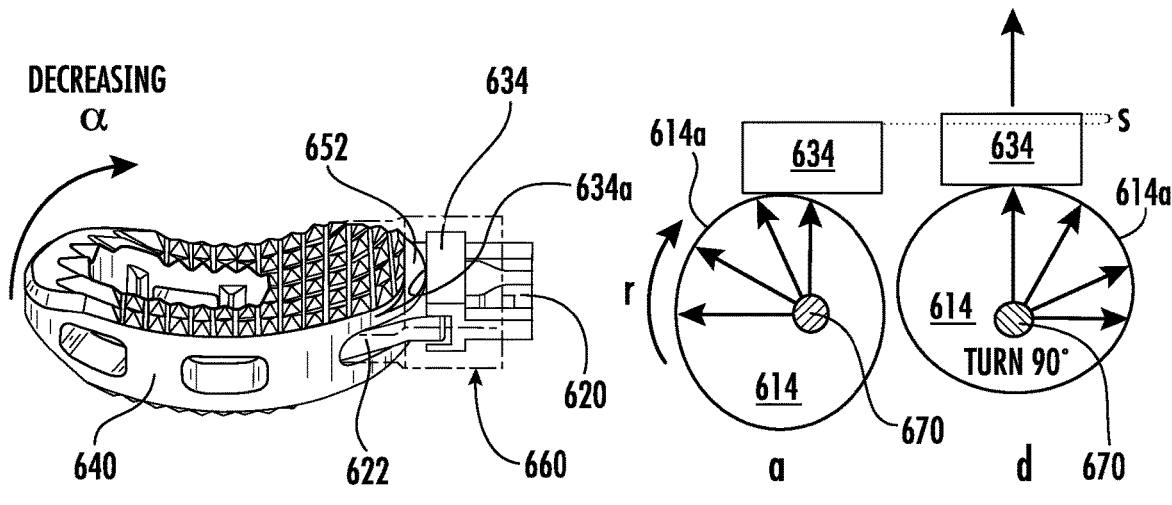
FIG. 6B
FIG. 7

SURGICAL IMPLANT POSITION DETECTION

BACKGROUND

Computer-assisted surgeries have many associated advantages, particularly in terms of placement precision of surgical tools and implants. While some computer-assisted surgical systems may have navigation and/or imaging capabilities for tracking placement of an implant, for example, certain views may be difficult to obtain, such as due to obstructions from patient anatomy. For example, certain types of implants are inserted into a patient adjacent to a bone, and then subsequently moved, for example, rotationally and/or translationally. In one such example, a transforaminal lumbar cage system (such as, for example, a transforaminal lumbar interbody fusion (TILF) cage system or a transforaminal posterior atraumatic lumbar (T-PAL™) cage system) requires an implant to be inserted into an incision and then pivoted into place beside a vertebrae as it advances. There is a need for a user (e.g., a surgeon) to determine how far the implant has pivoted.

Accordingly, there is a need for systems, devices, and methods for sensing or indicating a translational distance traveled by the implant.

SUMMARY

Systems, methods, and devices are disclosed for surgical systems comprising an applicator having a first shaft, an implant having a first member pivotably and detachably coupled to the first shaft, and a second member for converting rotational motion of the implant to a translational offset, and at least one of a sensor for determining the offset or an indicator for indicating the offset, provided that the indicator is not a protrusion located at an end of the applicator. In some embodiments, a controller is further provided, the controller configured to receive offset data from the sensor, determine an angle of the implant in a patient using dimensions of the implant and the offset, and display a current position of the implant relative to patient anatomy. In some embodiments, the applicator has a second shaft slidably disposed on the first shaft along an axis defined by a longitudinal axis of the applicator.

BRIEF DESCRIPTION OF THE DRAWINGS

FIG. 6A depicts a distal portion of another embodiment of an applicator and an implant;

FIG. 6B depicts the implant of FIG. 6A connected to the applicator;

FIG. 7 is a schematic of a pivoting motion of the implant of FIG. 6A being determined with a translational indicator;

DETAILED DESCRIPTION

Figure 1:
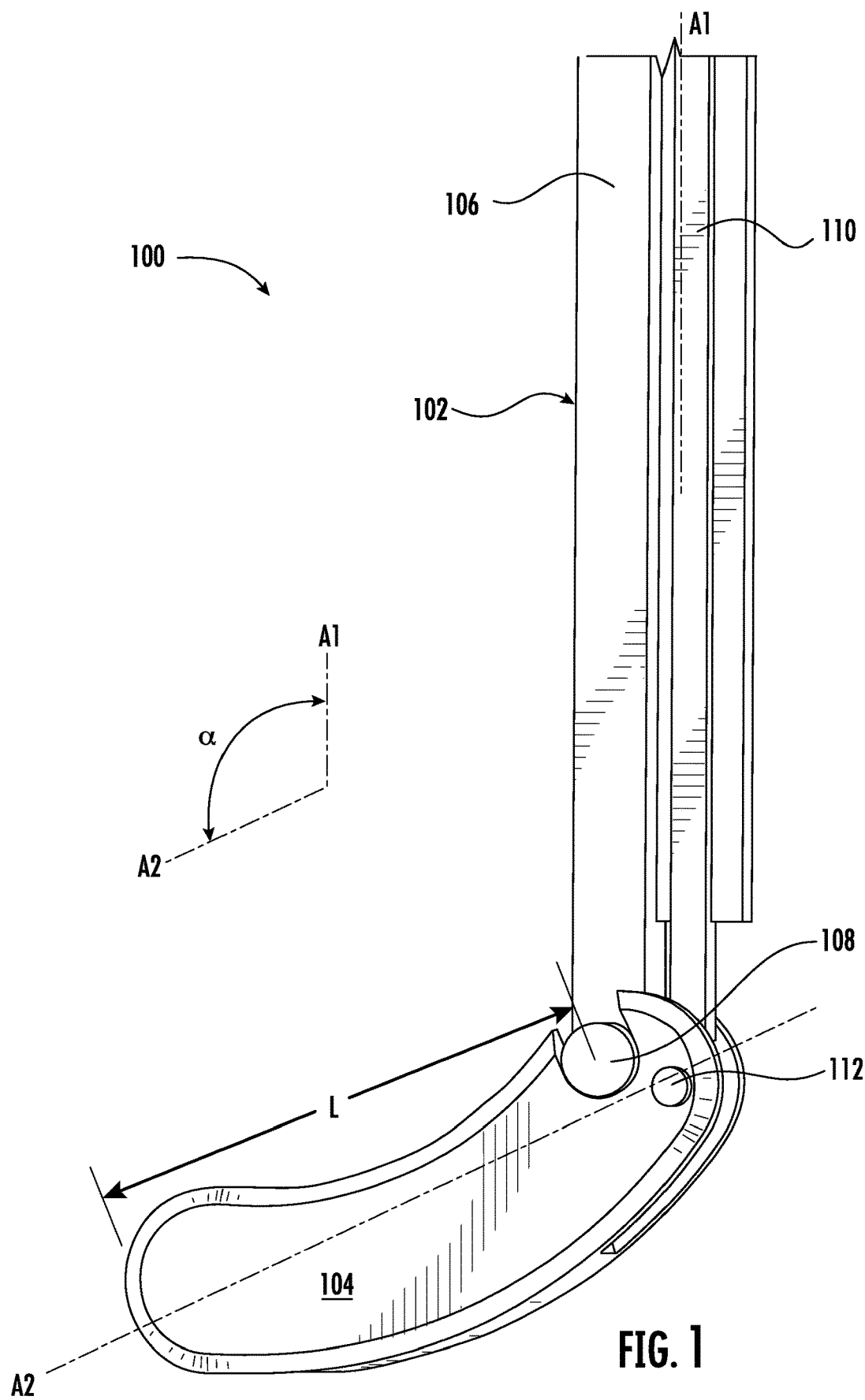
FIG. 1 shows a distal portion of a sensor-equipped applicator connected to an implant.

FIG. 1 shows an assembly 100 comprising an applicator 102 detachably and pivotably coupled to an implant 104. For simplicity of illustration, only a relatively distal portion of the applicator 102 is depicted. For example, in some embodiments, the entire portion of the depicted assembly 100 may be inserted into a patient in need of the implant 104. As such, it may be difficult or impossible to directly observe the orientation of the implant 104 from some angles as it is being inserted. For example, fluoroscopy may be used to observe the implant 104 from angles other than shown in FIG. 1, but due to the presence of vertebrae, fluoroscopy cannot be used to directly image the implant from the angle shown in FIG. 1 (e.g., an axial view), as will be apparent in FIG. 2.

The applicator 102 has a longitudinal axis A1 and the implant 104 has a longitudinal axis A2. An angle $\alpha$ is defined between the axis A1 and the axis A2. To reach a desired position according to a treatment plan, the implant is inserted into the patient, and as it advances, the implant pivots (e.g., translates) into the desired position. As the implant 104 pivots clockwise with respect to the applicator 102, angle $\alpha$ decreases. When implant 104 is in place, e.g., the angle $\alpha$ has reached the desired position, a user (e.g., a surgeon) detaches the implant from the applicator 102. Alternatively, as will be described, the implant 104 and the applicator 102 may be adapted to detach themselves (e.g., automatically) when the angle $\alpha$ has reached the desired position.

The applicator 102 comprises a first shaft 106 which connects to the implant 104 at a pivot point 108. The implant 104 has a known length L from the pivot point 108 to a distal end of the implant. The pivot point 108 may be achieved in a number of ways, such as cooperating features on the applicator 102 and the implant 104. The connection (e.g., between the first shaft 106 and the implant 104) is detachable. For example, the applicator 102 may have jaws (not visible in FIG. 1) that grasp a shaft (not visible in FIG. 1) of the implant 104 at a location corresponding to the pivot point 108. As the implant 104 pivots clockwise with respect to the applicator 102 (as angle $\alpha$ decreases), the implant pivots around pivot point 108 and the distal end of the implant translates.

The applicator 102 further comprises a second shaft 110 which is slidably disposed on the shaft 106, and capable of movement along the axis A1. The shaft 110 connects to the implant 104 at a pin 112. The pin 112 is spaced apart from the pivot point 108. As the implant 104 pivots around pivot point 108, not only does angle $\alpha$ change, but the position of the pin 112 changes. For example, if angle $\alpha$ decreases, the position of the pin 112 would move relatively downward in FIG. 1, and alternatively, if angle $\alpha$ increases, the position of the pin 112 would move relatively upward in FIG. 1. As can be appreciated, if the pin 112 were on the opposite side of the pivot point 108 (e.g., to the left rather than the right in FIG. 1), the relationship between the position of the pin 112 and the angle $\alpha$ would be the reverse, however, there would still be a relationship that could be used to extrapolate the position of the implant 104, as will be described.

Assuming that shaft 106 is static with respect to the axis A1, the movement of shaft 110 (e.g., with respect to shaft 106, the difference between the two being referred to herein as the offset) can be directly correlated to angle $\alpha$. As mentioned above, angle $\alpha$ can be (e.g., can also be) correlated to a position of the implant 104. For example, if the dimensions of the implant 104, such as the length L, a location of the pivot point 108, and a location of the pin 112 are known, the angle α may be determined (e.g., as a function of the offset), and used to determine if the desired position has been reached. Other features of the geometry of the implant 104 (e.g., curvature, tapers, etc.) may also be considered in determining whether the desired position has been reached.

One or more sensors (not depicted) may be operably attached to shaft 110 to determine the offset, e.g., between the shaft 106 and the shaft 110 or between another reference point and the shaft 110. In some embodiments, the sensor is not a direct visual scale, for example, such as a scale where the shaft 110 is directly marked and visually protrudes above shaft 106 by the offset.

The sensor may provide higher accuracy for offset determinations. The sensor may be located outside the patient's body. The sensor may be calibrated before surgery. The sensor may be a single-use sensor that attaches to the assembly 100, for example, as a click-on sensor. The sensor may be configured send a signal to transmit data. For example, the sensor may be selected from magnetic sensors, Hall effect sensors, stress sensors, strain sensors, spring sensors, Piezo sensors, distance sensors (such as light or infrared sensors), pneumatic pressure sensors, or hydraulic pressure sensors. Alternatively or additionally, if used in a computer assisted surgery (CAS) system, and if the implant 104 and the applicator 102 are navigated and therefore equipped with a tracker with markers (opto-electronic, magnetic, etc.) tracked with a corresponding camera, magnetic field sensor, etc., the applicator 102 may also receive an additional dynamic marker that can be used to determine the offset (e.g., representing the angulation) with respect to the fixed orientation of the marker tracker.

Those skilled in the art can configure such sensors to determine relative movement. The sensor may be wired or wirelessly connected to transmit data. Wired or wireless communication may be achieved over a variety of protocols, such as wireless (e.g., near-field communication (NFC), WIFI™, BLUETOOTH™, BLUETOOTH LE™, ZIGBEE™, and the like) or wired (e.g., USB or Ethernet). For example, the data may be actively communicated to a computer-assisted surgical system (e.g., a controller, etc.) or other navigation module. The data may be used to determine the offset, and the offset may be used to calculate the angle α, which in turn may be used to determine a position of the implant. An algorithm to calculate angle α and/or the position of the implant may take into account the geometry, including dimensions, of the implant 104.

Figure 2:
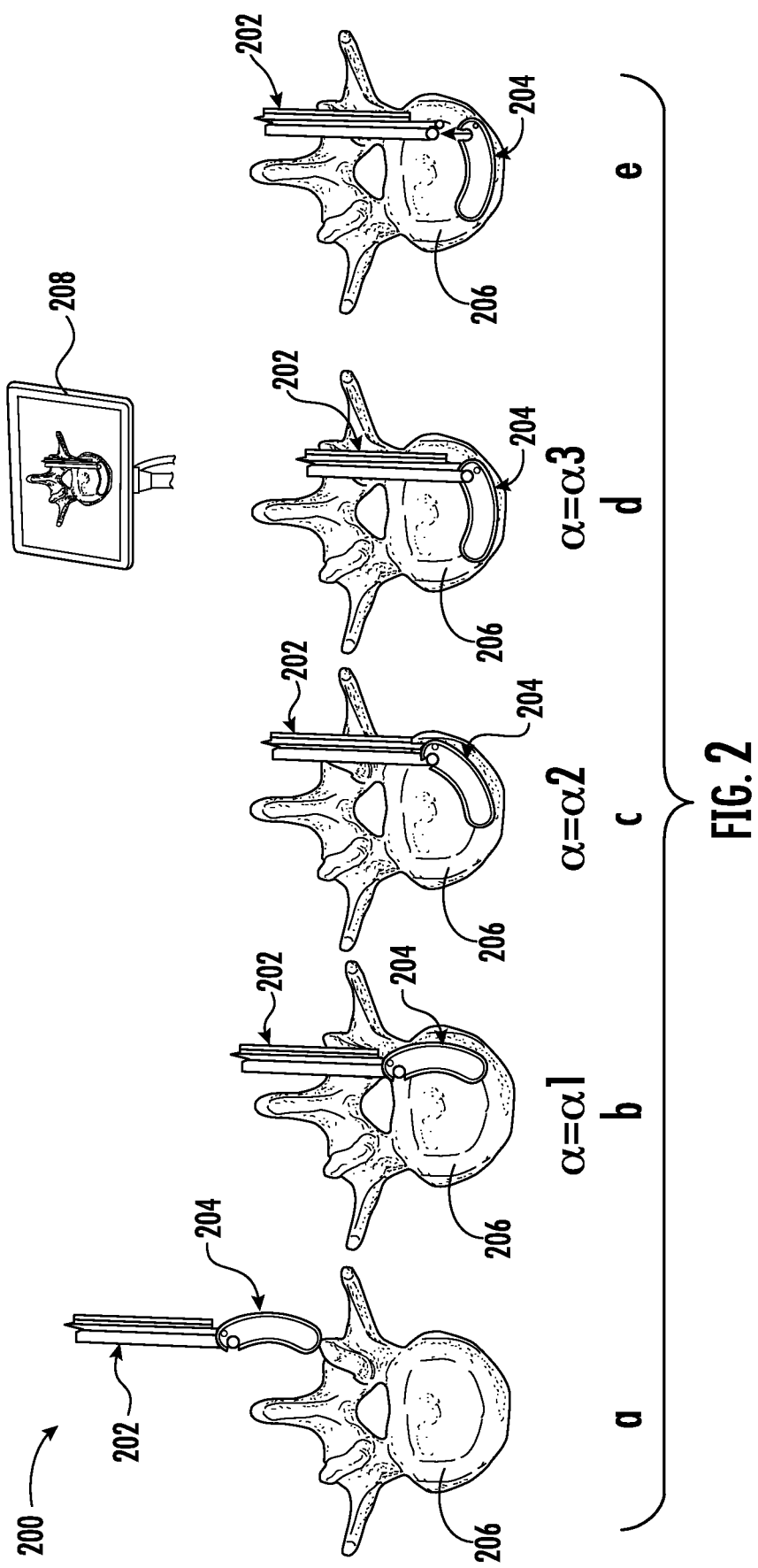
FIG. 2 shows a sequential insertion of an implant into a patient and a pivoting motion of the implant being determined with a translational sensor.

FIG. 2 shows a method 200 of inserting an implant 204 into a patient and determining a pivotal position of the implant with respect to an applicator 202. The applicator 202 and the implant 204 may be substantially similar to the applicator 102 and the implant 104 of FIG. 1 described above. The implant 204 may need to be positioned in the anterior aspects of the intervertebral space, adjacent a vertebra 206 of a patient, for example, in accordance with a treatment plan.

In step a, the applicator 202 and the implant 204 are detachably coupled together. A proximal end (not shown) of the applicator 202 may be equipped with a locking and/or release mechanism for coupling the implant 204 to the applicator 202. The respective axes of the applicator 202 and the implant 204 are somewhat similar in step a, accordingly, an angle α between the applicator and the implant is at a maximum (and thus, an offset defined between the applicator and the implant is at a maximum). A sensor (not depicted) such as described in FIG. 1, may be calibrated to determine the offset. The sensor may provide offset data to a control unit and display module 208 which may be used to determine angle α and model a placement of the implant 204 in the patient. The control unit and display module 208 may, in some embodiments, be multiple components, for example as described in FIG. 3.

The model displayed on the control unit and display module 208 may track the progress of the implant 204, e.g., in real time. Alternatively, the model displayed on the control unit and display module 208 may represent a properly installed implant 204 and may use the offset from the sensor to calculate a percentage of pivoting required before a final (e.g., the desired) position is achieved.

At step b, the implant 204 is inserted into the patient adjacent the vertebra 206. The proximal end (not shown) of the applicator 202 may be tapped or hammered to advance the implant 204 into the patient. A channel (not depicted) may be created in disc material adjacent the vertebra 206. At step b, the angle α between the applicator 202 and the implant 204 may be relatively large, represented in FIG. 2 as an angle α1. A general position of the implant 204 may be tracked by simultaneous methods. For example, fluoroscopy may also be used to observe the implant 204 from angles other than shown in FIG. 2, but due to the presence of vertebrae, fluoroscopy cannot be used to directly image the implant from the angle shown in FIG. 2 (e.g., an axial view).

At step c, the implant 204 is advanced farther into the patient. Due to a combination of the geometry of the implant 204, the anatomy of the patient, and the channel, the implant pivots as it is advanced (e.g., pivots with respect to a longitudinal axis defined by the applicator 202). At step c, as the implant 204 pivots, the angle α between the applicator 202 and the implant 204, represented in FIG. 2 as an angle α2, decreases, such that α1>α2.

At step d, the implant 204 is advanced farther into the patient and pivots as it is advanced, achieving its final (e.g., desired) position, represented in FIG. 2 as an angle α3. It is understood that α1>α2>α3. The control unit and display module 208 may be configured to provide an alert when the implant 204 reaches the desired position, for example, a user (e.g., a surgeon) may be alerted by the module. Proper placement may be confirmed in parallel, such as with fluoroscopy, if required.

At step e, a locking and/or release mechanism associated with the applicator 202 may be activated and the implant 204 uncoupled from the applicator.

Figure 3:
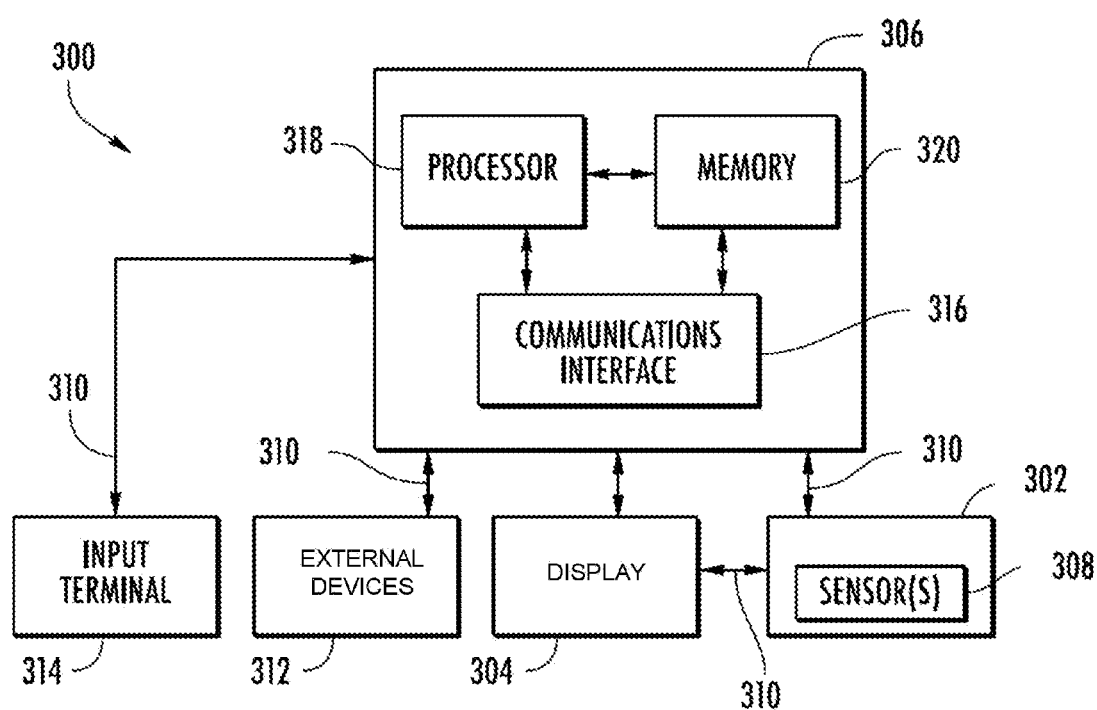
FIG. 3 is a schematic of a computer-assisted surgical system including a controller for use with a sensor.

FIG. 3 shows an overview of a computer-assisted surgical system 300 according to the present disclosure. The system 300 may include a sensor system 302, a display 304, and a controller 306. The sensor system 302 may include one or more sensors 308, such as any of the sensors described above, that are adapted to, or capable of, detecting or gathering data that may be indicative of offset.

A plurality of data paths 310, such as a wired or wireless data transmission path, may be used to communicatively couple the components of the system 300. For example, the controller 306 is communicatively coupled via a wired or wireless data transmission path 310 to the sensor system 302. In some embodiments, the controller 306 may be communicatively coupled via wired or wireless data transmission paths 310 to one or more external devices 312 and/or input terminals 314.

The controller 306 may include a communications interface 316, a processor 318, and a memory 320, each of which may be in communication with one another. Although each of these components are referred to in the singular, it will be appreciated that the various functions described as being carried out by one of the components may be carried out by multiple of these components, e.g., the functions described as being carried out by the processor 318 may be carried out by multiple processors, etc.

The controller 306 may receive data from the sensor system 302 and transmit data to the display 304 via the communications interface 316. As introduced above, in some embodiments, the controller 306 may communicate with one or more external device 312 and/or one or more input terminal 314. By way of non-limiting example, the external device 312 may be a computing device, remote server, etc. In some CAS embodiments, an image device connection (e.g., or the ability to upload patient image data or intra-op acquired patient data of the anatomy) is important for a navigation system to show the device (e.g., implant) with respect to the patient's anatomy.

The input terminal 314 may be configured to allow a surgeon or other user to input data directly into the controller 306. Such data may include patient information, surgical procedure information, implant dimensions, sensor type, and the like. The input terminal 314 may be any known input device, for example, a keyboard and/or cursor. The communication interface 316 may be wireless (e.g., near-field communication (NFC), Wi-Fi, Bluetooth, Bluetooth LE, ZigBee, and the like) or wired (e.g., USB or Ethernet). In some embodiments the communication interface may include one or more wireless and wired connections. In the case of a wireless connection, the communication interface 316 may be selected or programmed to provide a desired communication range. The communications interface 316 may receive data from the one or more sensors 308 via the communication path 310 (e.g., a physical signal transmission path or a wireless connection).

The sensors 308 may transmit data gathered or sensed regarding the offset to the communications interface 316. The data transmitted from the sensors 308 may include, but is not limited to, output from magnetic sensors, Hall effect sensors, stress sensors, strain sensors, spring sensors, Piezo sensors, distance sensors (such as light or infrared sensors), pneumatic pressure sensors, or hydraulic pressure sensors. The particular type of data transmitted to the controller 306 will depend on the type of sensor(s) 308 coupled to the applicator. The communications interface 316 may transmit the parameter data received from the sensors 308 to the memory 320 for storage and/or to the processor 318 for analysis. For example, the offset may be directly correlated to angle α. As mentioned above, angle α may be (e.g., may also be) correlated to a position of the implant. The processor 318 may determine the position considering, for example, the dimensions of the implant (e.g., such as the length L, a location of the pivot point, a location of an eccentric point, etc.). The processor 318 may determine the angle α (e.g., as a function of the offset). The processor 318 may determine if the desired position has been reached. The processor 318 may determine to send an alert to the display. The alert may (e.g., may also) include illumination of an LED or other visual alert on the external device 312 or other component of the system 300, the triggering of a chime sound, the logging of information in a connected server, external device, or computing system, etc.

The processor 318 may determine to model (e.g., and display) a placement of the implant in the patient. The model displayed on the display module 304 may track the progress of the implant, e.g., in real time. The processor 318 may determine to model (e.g., and display) a properly installed implant and may use the offset determined from the sensor (s) 308 to calculate a percentage of pivoting required before a final (e.g., the desired) position is achieved.

The processor 318 may include a microcontroller, a microcomputer, a programmable logic controller (PLC), a field-programmable gate array (FPGA), an application specific integrated circuit (ASIC), integrated circuits generally referred to in the art as a computer, and other programmable circuits, and these terms are used interchangeably herein.

Figure 4A:
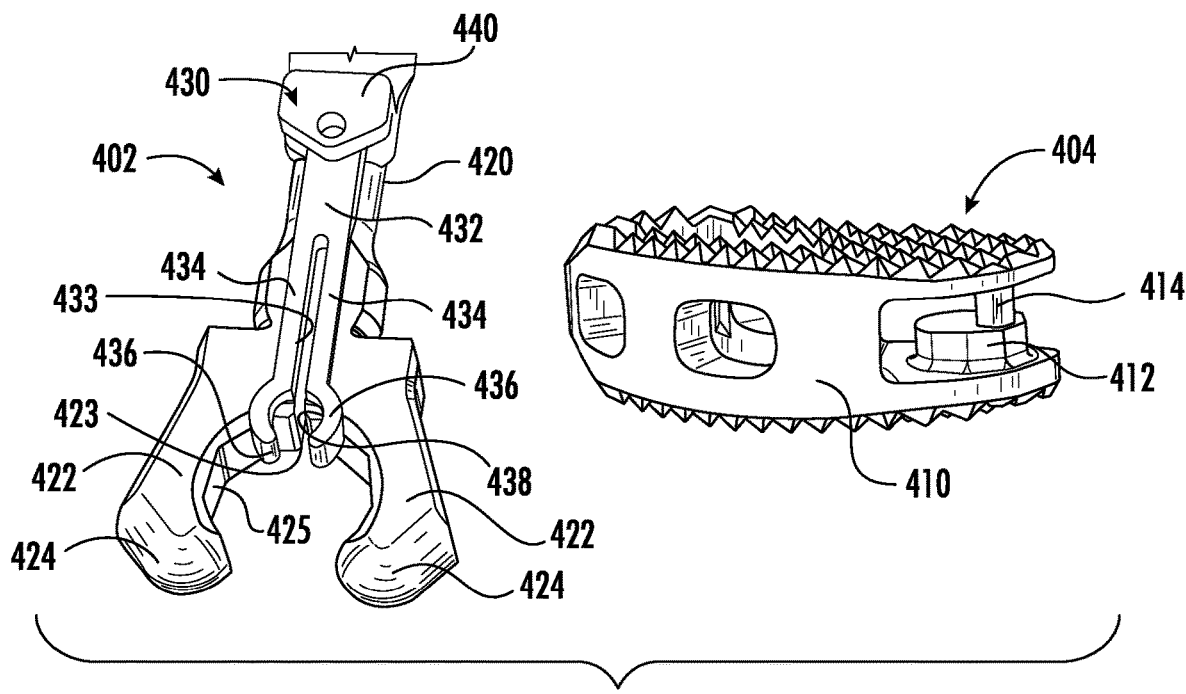
FIG. 4A depicts a distal portion of another embodiment of an applicator and an implant.
Figure 4B:
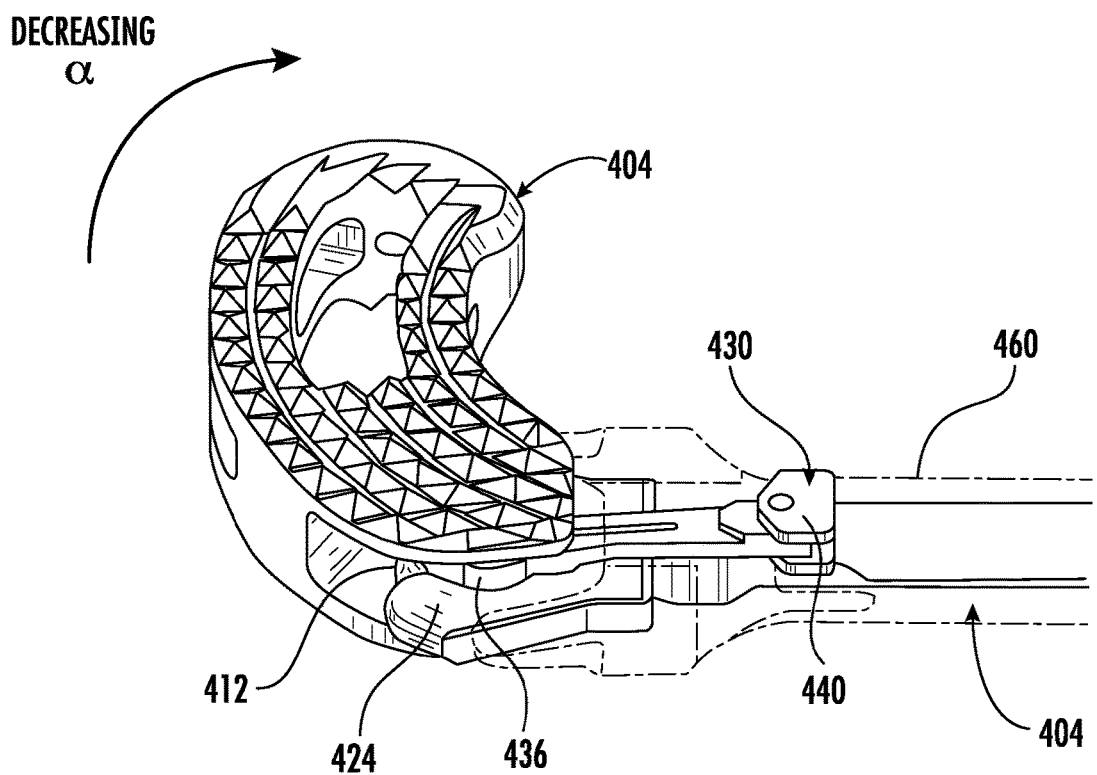
FIG. 4B depicts the implant of FIG. 4A connected to the applicator.

FIGS. 4A and 4B depict a distal portion of an applicator 402 and an implant 404. As is best seen in FIG. 4B, the applicator 402 detachably and pivotably couples to the implant 404. From a clinical perspective, the applicator 402 and the implant 404 may function substantially similarly to the applicator 102 and the implant 104 (FIG. 1) or the applicator 202 and the implant 204 (FIG. 2). The implant 404 is attached to the applicator 402, inserted into an incision in a patient (not depicted) in need thereof, and pivoted into place as it advances (e.g., toward a desired position). The applicator 402 has a longitudinal axis, the implant 404 has a longitudinal axis, and an angle α is defined between the axes. A predetermined angle α represents the desired position of the implant 404 in the patient according to a treatment plan. As the implant 404 pivots clockwise (e.g., as viewed in FIG. 4B) with respect to the applicator 402, the angle α decreases. After the implant 404 reaches the desired position, the implant is released from the applicator by a user (e.g., a surgeon).

As is best seen in FIG. 4A, the implant 404 comprises a body 410 having various features such as ridges and openings. At a proximal end of the body 410, a boss 412 is disposed. The boss 412 acts as a pivot point for the implant 404. The boss 412 is generally cylindrical, although depicted with facets. A pin 414 extends from the boss 412, and is disposed off-center relative to the boss. The eccentric placement of the pin 414 causes a translational movement of the pin when the implant 404 pivots around the boss 412.

For simplicity of illustration, only a relatively distal portion of the applicator 402 is depicted. A shaft 420 extends longitudinally and terminates in a pair of jaws 422. A channel 423 is defined in the shaft 420 between the jaws 422 in order to allow the jaws to move closer together or farther apart, for example, to engage or disengage with a portion of the implant 404 (e.g., the boss 412), as will be described. In an example, the motive force to move the jaws closer together (or farther apart) may be provided, for example, by turning a knob located on a relatively proximal portion of the applicator 402 (not depicted). For example, rotation of the knob in a first direction could close or lock the pair of jaws 422 to secure the implant 404, and rotation of the knob in a second direction could open or unlock the pair of jaws 422 to disengage or release the implant (or, alternatively, to initiate coupling).

A distal tip 424 is disposed at the end of each of the pair of jaws 422. The distal tips 424 and pair of jaws 422 cooperate to define an opening 425 for receiving and retaining the boss 412 of the implant 404. The size of the opening 425 varies with the position of the pair of jaws 422 (e.g., to engage or disengage with the boss 412 of the implant 404). It is contemplated that even when the implant 404 is locked or coupled to the applicator 402, the size of the opening 425 is still sufficiently large to allow the implant to pivot with respect to the applicator. As such, the center of the opening 425 aligns with the pivot point defined by the boss 412.

A second shaft 430 is slidably disposed on the shaft 420, and capable of movement along an axis defined by the shaft 420. A sheath 460 (FIG. 4B) may be provided to cover portions of the first shaft 420 and the second shaft 430.

A distal portion of the shaft 430 retains a bar 432. A channel 433 is defined in the bar 432 and divides the bar into a pair of arms 434. The channel 433 allows for some flexion in order to allow the arms 434 to move closer together or farther apart. A distal tip 436 is disposed at the end of each of the arms 434. The distal tips 436 and the arms 434 cooperate to define a second opening 438. The opening 438 receives the pin 414 (e.g., the arms 434 flex to receive the pin in the opening when the applicator 402 is coupled to the implant 404). The arms 434 retain the pin 414 in the opening 438 with sufficient force to allow translational movement of the pin to be transferred to the shaft 430. The force may be sufficient to pull the shaft 430 down the shaft 420 toward the implant 404, however, the force should not inhibit detachment of the implant 404 from the applicator 402. If necessary, the force can be calibrated or balanced by opposing forces.

For example, the arms 434 should not retain the pin 414 once the implant 404 is released from the applicator 402. It is possible that the applicator 402 being pulled away by the user (e.g., after opening or unlocking the pair of jaws 422 to release the boss 412 of the implant) may exert sufficient force to overcome the force exerted by the arms 434 retaining the pin 414. However, in some embodiments, features are provided to overcome the force exerted by the arms 434 retaining the pin 414. These features could be configured to operate before or concurrent with opening or unlocking the pair of jaws 422 to release the boss 412 of the implant 404.

For example, in some embodiments, a stop 440 is provided on the shaft 430 so that after a certain amount of translational movement of the shaft, the stop engages a surface (such as a surface on the shaft 420 or on the sheath 460) and further pivoting of the implant 404 causes the pin 414 to cam out of the opening 438.

In some embodiments, a wedge (not depicted) is provided on a non-moving surface (such as a surface on the shaft 420 or on the sheath 460) so that after a certain amount of translational movement of the shaft 430, the wedge enters the channel and forces the arms 434 apart, allowing the pin 414 to escape the opening 438.

An offset in translational movement between the first shaft 420 and the second shaft 430 can be correlated to an angle $\alpha$ defined between the axes of the applicator 402 and the implant 404. The offset (and/or angle $\alpha$) may be used to determine if the implant 404 has pivoted sufficiently to reach the desired position in the patient according to the treatment plan. As mentioned above, angle $\alpha$ (e.g., as a function of the offset) can be correlated to a position of the implant 404 using the dimensions of the implant, such as length L, location of the pivot point (boss 412), and/or location of the pin 414. Other features of the geometry of the implant 404 (e.g., curvature, tapers, etc.) may also be considered in determining whether the desired position has been reached.

While the sensor-based methods described with respect to FIGS. 1 & 2 may be used with the devices of FIGS. 4A & 4B (e.g., to determine the offset, for example, between the first shaft 420 and the second shaft 430 or between another reference point and the shaft 430), in some embodiments, the one or more sensors are replaced by an offset indicator. In some embodiments, the offset indicator is a direct visual scale, but it is not, for example, a scale where the shaft 430 is directly marked and visually protrudes above shaft 420 by the offset.

Figure 5:
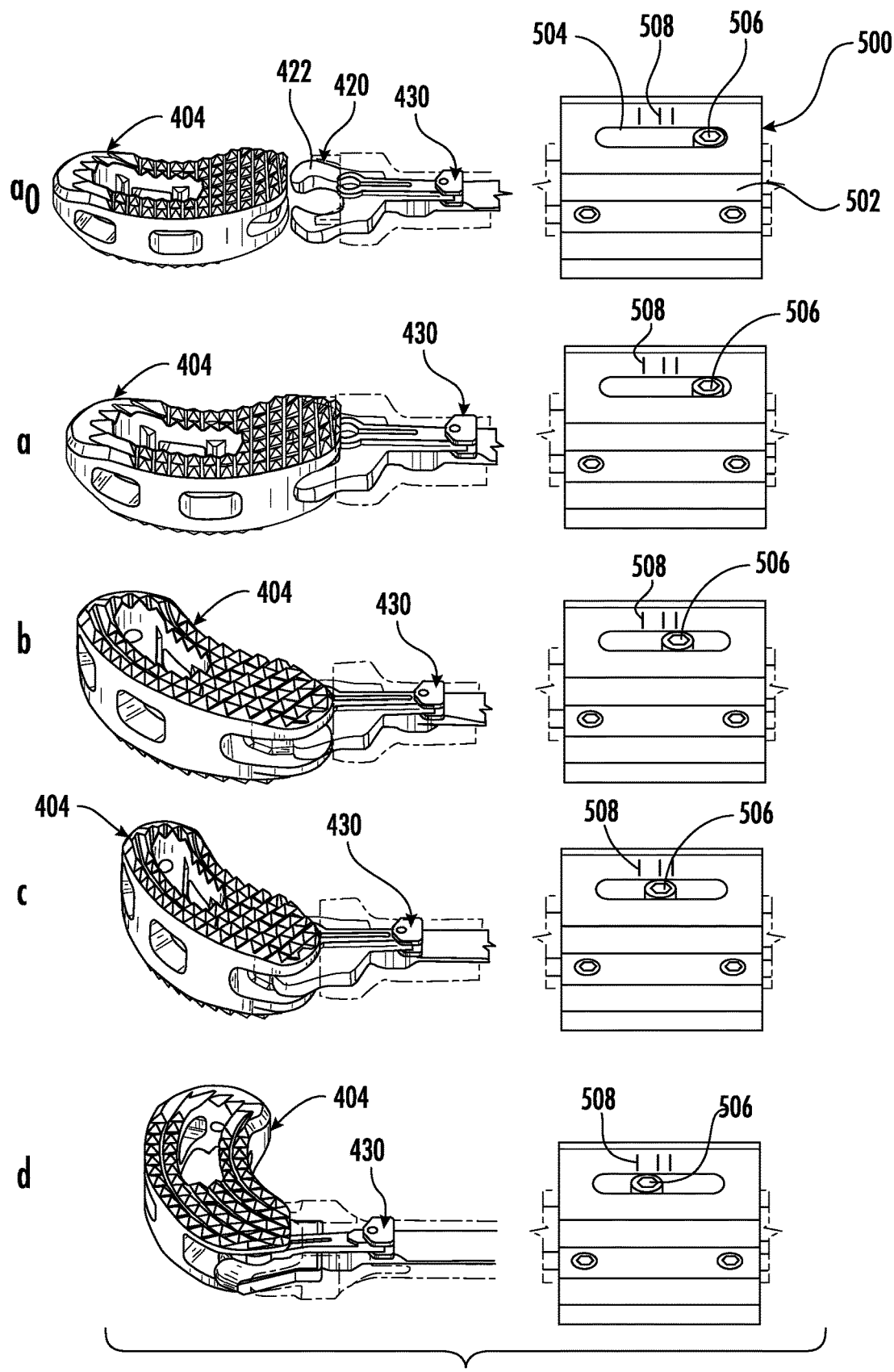
FIG. 5 is a schematic of a pivoting motion of the implant of FIG. 4A being determined with a translational indicator.

Turning to FIG. 5, the applicator 402 and the implant 404 are as described with respect to FIGS. 4A & 4B and the same reference numerals are used. An offset indicator 500 is connected to the applicator 402, but on a more proximal portion of the applicator that is located outside the patient's body. The offset indicator 500 has a housing 502. The housing 502 may be connected to the sheath 460, the shaft 420, or some other relatively stationary portion of the applicator 402. A channel 504 is defined by the housing 502.

A marker 506 is slidably disposed in the channel 504. The marker 506 is connected to the shaft 430, and thus, movement of the marker directly corresponds to movement of the shaft 430 (with reference to the stationary shaft 420), and hence, the offset. Indicia 508 are engraved or otherwise marked in the housing 502, and when aligned with the marker 506, the aligned indicium is indicative of a predetermined (for example, calibrated) position of the implant 404, such as an angle $\alpha$ associated with the position. A user (e.g., a surgeon) may use the indicium (e.g., one of the indicia 508) aligned with the marker 506 to gauge the progress of the surgical procedure. For example, as depicted in FIG. 5, the farther the marker 506 moves to the left, the closer the implant 404 is to the desired position.

In operation, the implant 404 may need to be positioned in the anterior aspects of the intervertebral space, adjacent a vertebra of a patient, for example, in accordance with a treatment plan. A general position of the implant 404 may be tracked by simultaneous methods, such as by fluoroscopy.

In step $a_0$, the applicator 402 is advanced toward the implant 404. The pair of jaws 422 of the applicator 402 are at a position where they are farthest apart from each other. As mentioned previously, the motive force to move the jaws closer together could be provided, for example, by turning a knob located on a relatively proximal portion of the applicator 402 (not depicted). For example, the pair of jaws 422 would be opened or unlocked before the user attempted to couple the implant 404 to the applicator. The marker 506 of the indicator 500 may be in a first position, such as to reflect a base or initial position of the shaft 430.

In step a, the applicator 402 and the implant 404 are detachably coupled together, e.g., the boss 412 (FIG. 4A) of the implant 404 is captured in the opening 425 defined between the pair of jaws 422. Also, the pin 414 (FIG. 4A) of the implant 404 is received in the opening 438 (FIG. 4A) of the shaft 430. The respective axes of the applicator 402 and the implant 404 are somewhat similar in step a, accordingly, an angle $\alpha$ between the applicator and the implant is at a maximum (and thus, an offset defined between the applicator and the implant is at a maximum). The marker 506 of the indicator 500 may remain in the first position, such as to reflect the base or initial position of the shaft 430 (e.g., the shaft may not move until the implant 404 begins to pivot).

At step b, the implant 404 is inserted into the patient (not shown), such as in a channel created in disc material adjacent to a vertebra. The proximal end (not shown) of the applicator 402 may be tapped or hammered to advance the implant 404 into the patient. Due to a combination of the geometry of the implant 404, the anatomy of the patient, and the channel, the implant pivots as it is advanced (e.g., pivots with respect to a longitudinal axis defined by the applicator 402). At step b, the angle $\alpha$ between the applicator 402 and the implant 404 may be smaller than at step a, but still relatively large, represented by the marker 506 of the indicator 500 reaching the indicia 508. Movement of the marker 506 is effected by the pin 414 (FIG. 4A) of the implant 404 pulling the shaft 430 in the direction of the implant as the implant pivots, the pin being eccentric to a pivot point of the implant.

At step c, the implant 404 is advanced farther into the patient and the implant continues to pivot. The offset between the shaft 420 and the shaft 430 decreases (e.g., as the implant 404 continues to pivot). As the implant 404 continues to pivot, the pin 414 (FIG. 4A) of the implant pulls the shaft 430 farther in the direction of the implant, represented by the marker 506 of the indicator 500 reaching a middle indicium of the indicia 508.

At step d, the implant 404 is advanced farther into the patient (pivoting as it advanced), achieving its final (e.g., desired) position. The implant 404 pulls the shaft 430 farther in the direction of the implant, represented by the marker 506 of the indicator 500 reaching a desired position indicium of the indicia 508. The user (e.g., the surgeon) may use the indicator 500 to determine that the implant 404 has reached the desired position. Proper placement may be confirmed in parallel, such as with fluoroscopy, if required.

Although not depicted, the user (e.g., the surgeon) may determine to release the implant 404 from the applicator 402 by activating a locking and/or release mechanism associated with the applicator and the implant may be uncoupled from the applicator. For example, the implant may be released by turning a knob located on a relatively proximal portion of the applicator 402 (not depicted). The locking and/or release mechanism may cause the opening 425 (FIG. 4A) defined between the pair of jaws 422 to be widened such that the boss 412 (FIG. 4A) of the implant 404 is no longer retained in the opening. The applicator 402 may be drawn back away from the implant 404. The pin 414 (FIG. 4A) may escape the arms 434 (FIG. 4A) of the shaft 430, such as after release, e.g., by the force of the applicator 402 being drawn back away from the implant 404, or previous to or concurrent with release, such as by the pin camming out of the arms or the arms being driven apart to allow the pin to pass.

FIGS. 6A and 6B depict a distal portion of an applicator 602 and an implant 604. As is best seen in FIG. 6B, the applicator 602 detachably and pivotably couples to the implant 604. From a clinical perspective, the applicator 602 and the implant 604 may function substantially similarly to the previous described applicators and implants, e.g., the implant 604 is attached to the applicator 602, inserted into an incision in a patient (not depicted) in need thereof, and pivoted into place as it advances (e.g., toward a desired position). The applicator 602 has a longitudinal axis, the implant 604 has a longitudinal axis, and an angle α is defined between the axes. A predetermined angle α represents the desired position of the implant 604 in the patient according to a treatment plan. As the implant 604 pivots clockwise (e.g., as viewed in FIG. 6B) with respect to the applicator 602, the angle α decreases. After the implant 604 reaches the desired position, the implant is released from the applicator by a user (e.g., a surgeon).

As is best seen in FIG. 6A, the implant 604 comprises a body 610 having various features such as ridges and openings. At a proximal end of the body 610, a boss 612 is disposed. The boss 612 acts as a pivot point for the implant 604. The boss 612 is generally cylindrical, although depicted with facets. A cam 614 extends above the boss 612, and is disposed off-center relative to the boss, for example, a portion of the cam may protrude farther from the body 610 on a first side of the boss. The eccentric placement of the cam 614 causes a translational movement of a surface 614a of the cam when the implant 604 pivots around the boss 612.

For simplicity of illustration, only a relatively distal portion of the applicator 602 is depicted. A shaft 620 extends longitudinally and terminates in a pair of jaws 622. A channel 623 is defined in the shaft 620 between the jaws 622 in order to allow the jaws to move closer together or farther apart, for example, to engage or disengage with a portion of the implant 604 (e.g., the boss 612), as will be described. In an example, the motive force to move the jaws closer together (or farther apart) may be provided, for example, by turning a knob located on a relatively proximal portion of the applicator 602 (not depicted). For example, rotation of the knob in a first direction could close or lock the pair of jaws 622 to secure the implant 604, and rotation of the knob in a second direction could open or unlock the pair of jaws 622 to disengage or release the implant (or, alternatively, to initiate coupling).

A distal tip 624 is disposed at the end of each of the pair of jaws 622. The distal tips 624 and pair of jaws 622 cooperate to define an opening 625 for receiving and retaining the boss 612 of the implant 604. The size of the opening 625 varies with the position of the pair of jaws 622 (e.g., to engage or disengage with the boss 612 of the implant 604). It is contemplated that even when the implant 604 is locked or coupled to the applicator 602, the size of the opening 625 is still sufficiently large to allow the implant to pivot with respect to the applicator. As such, the center of the opening 625 aligns with the pivot point defined by the boss 612.

A second shaft 630 is slidably disposed on the shaft 620, and capable of movement along an axis defined by the shaft 620. A distal portion of the shaft 630 comprises a pair of arms 632 attached by a distal end 634. The end 634 has a surface 634a that acts as a cam follower in relation to the cam 614 (e.g., the end surface 634a is biased against the surface 614a of the cam 614 (e.g., such as by springs) when the applicator 602 is coupled to the implant 604. The biasing force may facilitate detachment of the implant 604 from the applicator 602. A sheath 660 (FIG. 6B) may be provided to cover portions of the first shaft 620 and the second shaft 630.

Pivoting of the implant 604 allows translational movement of the surface 614a of the cam 614 to be transferred to the shaft 630. As is best seen in FIGS. 6B and 7, if angle α decreases (clockwise rotation r in FIG. 7) such as by pivoting around a pivot point 670 (e.g., a theoretical pivot point running through the boss 612), the position of the surface 614a moves relatively rightwards (FIG. 6B, e.g., upwards by offsets in FIG. 7). As can be appreciated, if the surface 614a were on the opposite side of the pivot point defined by the boss 612 (e.g., to the front rather than the back in FIG. 6B), the relationship between the position of the surface and the angle α would be the reverse, however, there would still be a relationship that could be used to extrapolate the position of the implant 604. Due to the eccentric shape of the cam 614 in relation to a pivot point 670 (e.g., defined by the boss 612), the shaft 630 is forced to move relative to shaft 620 as the implant 604 pivots (e.g., while being advanced into the patient).

An offset in translational movement between the first shaft 620 and the second shaft 630 can be correlated to an angle α defined between the axes of the applicator 602 and the implant 604, and thus used to determine if the implant 604 has pivoted sufficiently to reach the desired position in the patient according to the treatment plan. As mentioned above, angle α (e.g., as a function of the offset) can be correlated to a position of the implant 604 using the dimensions of the implant, such as length L, location of the pivot point 670 (e.g., within the boss 612), and/or location of the cam 614. Other features of the geometry of the implant 604

(e.g., curvature, tapers, etc.) may also be considered in determining whether the desired position has been reached.

While the sensor-based methods described with respect to FIGS. 1 & 2 may be used with the devices of FIGS. 6A & 6B (e.g., to determine the offset, for example, between the first shaft 620 and the second shaft 630 or between another reference point and the shaft 630), in some embodiments, the one or more sensors are replaced by an offset indicator. In some embodiments, the offset indicator is a direct visual scale, but it is not, for example, a scale where the shaft 630 is directly marked and visually protrudes above shaft 620 by the offset.

Figure 8:
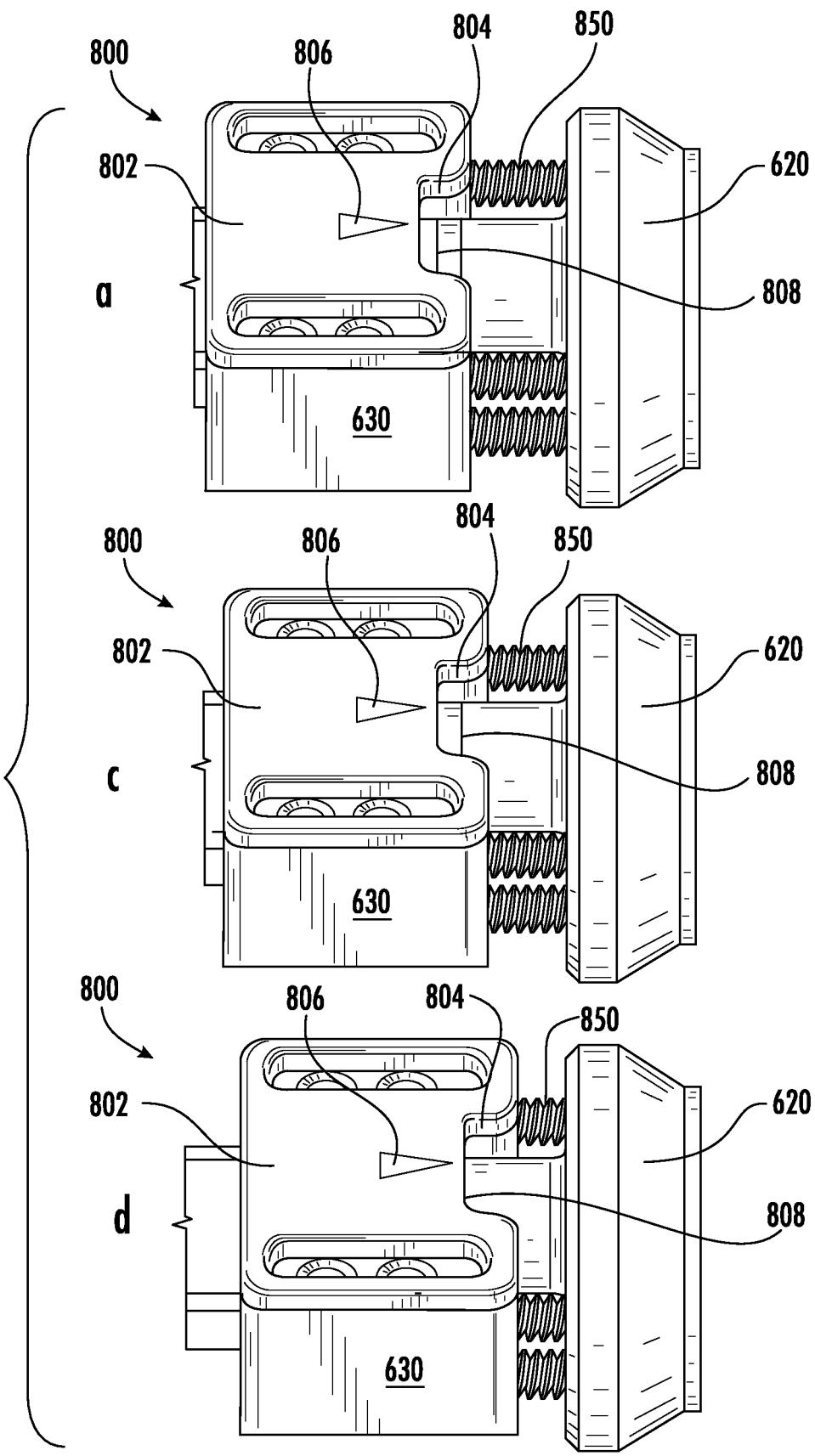
FIG. 8 depicts another embodiment of an indicator.

Turning to FIG. 8, features of the first shaft 620 and the second shaft 630 of the applicator 602 are as described with respect to FIGS. 6A & 6B and the same reference numerals are used. An offset indicator 800 is connected to the applicator 602, but on a more proximal portion of the applicator that is located outside the patient's body. The offset indicator 800 has a housing 802. The housing 802 is connected to the shaft 630, and thus, movement of the housing directly corresponds to movement of the shaft (with reference to the stationary shaft 620). A cut-out 804 is defined by the housing 802. A marker 806 is engraved or otherwise marked on the housing 802 adjacent to the cut-out 804.

Indicia 808 are engraved or otherwise marked on the first shaft 620. Alternatively, the indicia 808 may be on the sheath 660 or some other relatively stationary portion of the applicator 602. When aligned with the marker 806, the aligned indicium (e.g., of the indicia 808) is indicative of a predetermined (for example, calibrated) position of the implant 604, such as an angle α associated with the position. A user (e.g., a surgeon) may use the indicium (e.g., one of the indicia 808) aligned with the marker 806 to gauge the progress of the surgical procedure. For example, as depicted in FIG. 8, the farther the marker 806 moves to the right, the closer an implant (such as the implant 604) is to the desired position.

A set of springs 850 may be interposed between the first shaft 620 and the second shaft 630. The springs 850 bias the end 634 (FIG. 6A) of the shaft 630 against the cam 614 (FIG. 6A) of the implant 604 so that they abut. The surface 634a (FIG. 6A) acts as a cam follower in relation to the surface 614a of the cam 614 as the implant 604 pivots.

In operation, an implant (such as the implant 604) may need to be positioned in the anterior aspects of the intervertebral space, adjacent a vertebra of a patient, for example, in accordance with a treatment plan. A general position of the implant may be tracked by simultaneous methods, such as by fluoroscopy.

In step a, an applicator (such as the applicator 602) and the implant may be detachably coupled together, e.g., the boss 612 (FIG. 6A) of the implant 604 is captured in the opening 625 defined between the pair of jaws 622. Also, the cam 614 (FIG. 6A) of the implant 604 is abutting the end 634 (FIG. 6A) of the shaft 630 due to the action of the springs 850. The respective axes of the applicator and the implant may be somewhat similar in step a, accordingly, an angle α between the applicator and the implant is at a maximum (and thus, an offset defined between the applicator and the implant is at a maximum). The marker 806 of the indicator 800 is in a first position, such as to reflect a base or initial position of the shaft 630 (e.g., the shaft may not move until the implant begins to pivot).

At step c, the implant has been inserted into the patient (not shown), such as in a channel created in disc material adjacent to a vertebra. The proximal end (not shown) of the applicator 602 may be tapped or hammered to advance the implant 604 into the patient. Due to a combination of the geometry of the implant 604, the anatomy of the patient, and the channel, the implant pivots as it is advanced (e.g., pivots with respect to a longitudinal axis defined by the applicator). At step c, the angle α between the applicator 602 and the implant 604 may be considerably smaller than at step a, represented by the marker 806 of the indicator 800 reaching a middle indicium of the indicia 808. Movement of the marker 806 is effected by the cam 614 (FIG. 6A) of the implant 604 pushing the shaft 630 in a direction away from the implant as the implant pivots, the cam being eccentric to a pivot point of the implant. Stated differently, the offset between the shaft 620 and the shaft 630 decreases as the implant pivots.

At step d, the implant is advanced farther into the patient (pivoting as it advances), achieving its final (e.g., desired) position. The implant pushes the shaft 630 in a direction away from the implant as the implant pivots, represented by the marker 806 of the indicator 800 reaching a desired position indicium of the indicia 808. The user (e.g., the surgeon) may use the indicator 800 to determine that the implant has reached the desired position. Proper placement may be confirmed in parallel, such as with fluoroscopy, if required.

Although not depicted, the user (e.g., the surgeon) may determine to release the implant from the applicator by activating a locking and/or release mechanism associated with the applicator and the implant may be uncoupled from the applicator. For example, the implant may be released by turning a knob located on a relatively proximal portion of the applicator (not depicted). The locking and/or release mechanism may cause the opening 625 (FIG. 6A) defined between the pair of jaws 622 to be widened such that the boss 612 of the implant 604 is no longer retained in the opening. The applicator may be drawn back away from the implant. The cam 614 (FIG. 6A) may no longer abut the shaft 630 after release. In some embodiments, the springs 850 may partially assist with release by exerting pressure on the implant via the end surface 634a of the shaft 630.

Figure 9:
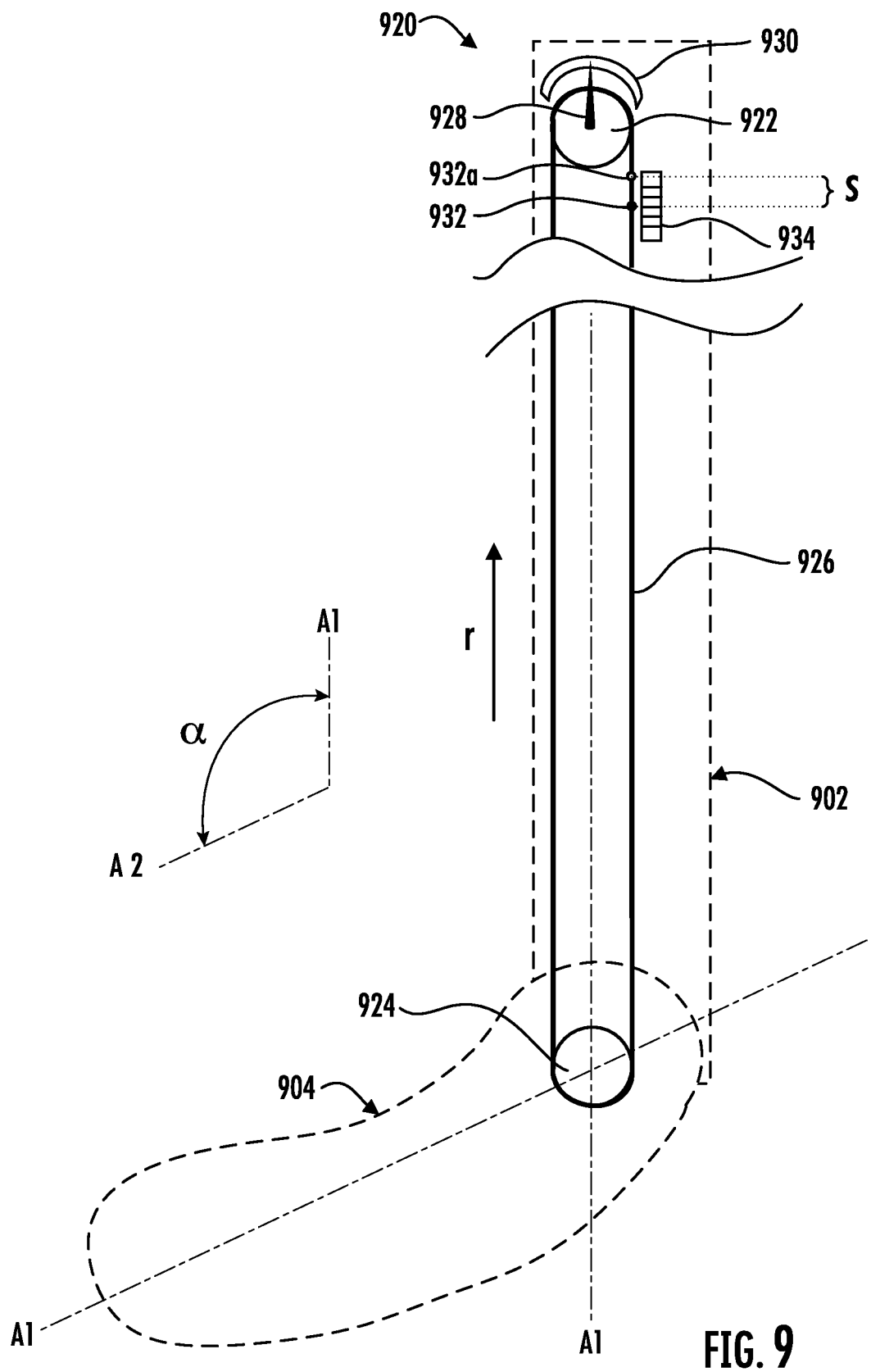
FIG. 9 depicts another embodiment of an indicator.

FIG. 9 depicts another embodiment of an indicator system, the system 920 being for use with an applicator 902 and an implant 904. The applicator 902 is detachably and pivotably coupled to an implant 904. A connection point (not depicted) between the applicator 902 and the implant 904 may be disposed at an internal portion of the implant. The applicator 902 has a longitudinal axis A1 and the implant 904 has a longitudinal axis A2. An angle α is defined between the axis A1 and the axis A2. To reach a desired position according to a treatment plan, the implant is inserted into the patient, and as it advances, the implant pivots (e.g., translates) into the desired position. As the implant 904 pivots clockwise with respect to the applicator 902, angle α decreases. When implant 904 is in place, e.g., the angle α has reached the desired position, a user (e.g., a surgeon) detaches the implant from the applicator 902.

A pulley 922 is disposed on the applicator 902. A non-rotatable protrusion 924 is associated with the implant 904, e.g., disposed at an external portion of the implant. The protrusion 924 may be integral to the implant 904 or may engage a recess (not depicted) in the implant, provided that the protrusion is detachable when the applicator is disengaged from the implant. The protrusion 924 is located at an intersection of the axis A1 and the axis A2, which corresponds to a pivot point of the implant 904. As the implant 904 pivots clockwise with respect to the applicator 902, the implant pivots around the internal connection point aligned with the pivot point. A wire loop 926 connects the pulley 922 and the protrusion 924. Pivoting of the implant 904 causes the wire loop 926 to rotate (e.g., clockwise rotation r), which rotates the pulley 922.

In some embodiments, a marker 928 is disposed on the pulley 922. Rotation of the pulley 922 results in movement of the marker 928. Indicia 930 are engraved or otherwise marked on the applicator or another stationary surface. It is understood that physical/visual indicators are only one example (e.g., sensors of various kinds can be used to measure the position of 928 of the rotation angle of the pulley 922 and output may be adapted accordingly).

When aligned with the marker 928, the indicia 930 are indicative of a predetermined (for example, calibrated) position of the implant 904, such as an angle α associated with the position. A user (e.g., a surgeon) may use the indicia 930 aligned with the marker 928 to gauge the progress of the surgical procedure. For example, as depicted in FIG. 9, the farther the marker 928 moves to the right, the closer the implant 904 is to the desired position. The position of the marker 928 may be correlated to a position of the implant 904. For example, if the dimensions of the implant 904 (e.g., such as length L, location of the pivot point, curvature, tapers, etc.), dimensions of the pulley 922 (e.g., such as width), dimensions of the marker 928 (e.g., such as length) are known, the indicia 930 may be adapted to reflect various positions of the implant, and used to determine if the desired position has been reached.

In some embodiments, a marker 932 is disposed on the wire loop 926. Rotation of the wire loop 926 results in movement of the marker 932 (e.g., from a previous position 932a to a current position represented by 932). Indicia 934 are engraved or otherwise marked on the applicator or another stationary surface. When aligned with the marker 932, the indicia 934 are indicative of a predetermined (for example, calibrated) position of the implant 904, such as an offset s representing travel of the wire loop 926. The offset s may be associated with an angle α which may in turn be associated with the position of the implant 904. A user (e.g., a surgeon) may use the indicia 934 aligned with the marker 932 to gauge the progress of the surgical procedure. For example, as depicted in FIG. 9, the farther the marker 932 moves downward, the closer the implant 904 is to the desired position. The position of the marker 932 may be correlated to a position of the implant 904. For example, if the dimensions of the implant 904 (e.g., such as length L, location of the pivot point, curvature, tapers, etc.), dimensions of the pulley 922 (e.g., such as width), dimensions of the wire loop (e.g., such as length) are known, the indicia 934 may be adapted to reflect various positions of the implant, and used to determine if the desired position has been reached. As noted, sensors could be used in conjunction with or alternatively to measure offset s. In some embodiments, both marker systems are used. After reaching the desired position the wire loop 926 may be slipped off the pulley 922 and then slipped off the protrusion 924. Alternatively, the marker 932 may be adapted to reversibly clamp the wire loop 926 into a loop and may be unclamped and the wire threaded around the protrusion 924 to release the implant 904 (e.g., before or after the user detaches the implant from the applicator 902).

Examples of the above-described embodiments may include the following.

In a first example, a surgical system comprises an applicator having a first shaft, an implant having a first member pivotably and detachably coupled to the first shaft, and a second member for converting rotational motion of the implant to a translational offset, and at least one of a sensor for determining the offset, or an indicator for indicating the offset, provided that the indicator is not a protrusion located at an end of the applicator.

In some embodiments, the second member is eccentric to a pivot point of the implant.

In some embodiments, the applicator further comprises a second shaft slidably disposed on the first shaft along an axis defined by a longitudinal axis of the applicator. In an example, the second member engages the second shaft, and wherein pivoting of the implant results in movement of the second shaft relative to the axis. In another example, the first member and the second member are internal to an outer surface of the implant.

In some embodiments, the sensor is a magnetic sensor, a Hall effect sensor, a stress sensor, a strain sensor, a spring sensor, a Piezo sensor, a distance sensor, a pneumatic pressure sensor, an opto-electronic measurement system marker, or a hydraulic pressure sensor.

In some embodiments, the second member is a pin and a distal portion of the second shaft is adapted to trap the pin. In an example, the indicator comprises a marker attached to the second shaft and indicia marked on a housing attached to the first shaft.

In some embodiments, the second member is a cam and a distal portion of the second shaft is adapted to follow the cam. In an example, the indicator comprises a marker attached to the second shaft and indicia marked on the first shaft. The embodiment further comprises springs to bias the second shaft toward the implant.

In some embodiments, the second member is concentric to a pivot point of the implant. In an example, the first member is internal to an outer surface of the implant and the second member is external to the outer surface of the implant, and the offset is translated to a wire loop attached between the second member and the applicator.

In a second example, a computer-assisted surgical system, comprises a controller configured to receive offset data from the sensor of any of the above described surgical system, determine an angle of the implant in a patient using dimensions of the implant and the offset, and display a current position of the implant relative to patient anatomy. In an example, the controller is further configured determine if a desired position has been reached and to display a notification to a user. In an example, the controller receives data from a tracker with markers (opto-electronic, magnetic, etc.) tracked with a corresponding camera, magnetic field sensor, etc., and an additional dynamic marker that can be used to determine the offset (e.g., representing the angulation) with respect to the fixed orientation of the marker tracker.

In a third example, a surgical system comprises an applicator having a first shaft and a second shaft slidably disposed on the first shaft along an axis defined by a longitudinal axis of the applicator, an implant having a first member pivotably and detachably coupled to the first shaft, and a second member eccentric to a pivot point of the implant for engaging the second shaft, wherein pivoting of the implant results in an offset of the second shaft along the axis, and at least one of a sensor for determining the offset or an indicator for indicating the offset, provided that the indicator is not a protrusion located at an end of the applicator. In an example, the sensor is a magnetic sensor, a Hall effect sensor, a stress sensor, a strain sensor, a spring sensor, a Piezo sensor, a distance sensor, a pneumatic pressure sensor, an opto-electronic measurement system marker, or a hydraulic pressure sensor. In an example, the indicator comprises a marker attached to the second shaft and indicia associated with the first shaft. In an example, the second shaft does not extend past the first shaft. In an example, the second member is not attached to the second shaft.

The invention claimed is:

1. A surgical system, comprising:
an applicator having a first shaft and a second shaft slidably disposed on the first shaft along an axis defined by a longitudinal axis of the applicator;
an implant having:
a first member comprising a boss pivotably and detachably coupled to the first shaft; and
a second member extending eccentrically from the boss for converting rotational motion of the implant to a translational offset, wherein the second member is a pin and a portion of the second shaft comprises a pair of arms adapted to trap the pin, and wherein the second member engages the second shaft, causing the second shaft to move relative to the first shaft during rotational motion of the implant; and
at least one of: a sensor for determining the offset, or an indicator comprising a marker attached to the second shaft for indicating the offset, provided that the indicator is not a protrusion located at an end of the applicator.

2. The system of claim 1, wherein the second member is eccentric to a pivot point of the implant.

3. The system of claim 1, wherein pivoting of the implant results in movement of the second shaft along the longitudinal axis.

4. The system of claim 1, wherein the first member and the second member are internal to an outer surface of the implant.

5. The system of claim 1, wherein the sensor is a magnetic sensor, a Hall effect sensor, a stress sensor, a strain sensor, a spring sensor, a piezoelectric sensor, a distance sensor, a pneumatic pressure sensor, an opto-electronic measurement system marker, or a hydraulic pressure sensor.

6. The system of claim 1, wherein the indicator further comprises indicia marked on a housing attached to the first shaft.

7. A computer-assisted surgical system, comprising:
a controller configured to:
receive offset data from the sensor of the surgical system of claim 1;
determine an angle of the implant in a patient using dimensions of the implant and the offset; and
display a current position of the implant relative to patient anatomy.

8. The computer-assisted surgical system of claim 7, wherein the controller is further configured determine if a desired position has been reached and to display a notification to a user.

9. A surgical system, comprising:
an applicator having a first shaft and a second shaft slidably disposed on the first shaft along an axis defined by a longitudinal axis of the applicator;
an implant having:
a first member comprising a boss pivotably and detachably coupled to the first shaft; and
a second member extending eccentrically from the boss for engaging the second shaft, wherein the second member is a pin and a portion of the second shaft comprises a pair of arms adapted to trap the pin, and wherein pivoting of the implant results in an offset of the second shaft along the axis; and
at least one of a sensor for determining the offset or an indicator comprising a marker attached to the second shaft for indicating the offset, provided that the indicator is not a protrusion located at an end of the applicator.

10. The system of claim 9, wherein the sensor is a magnetic sensor, a Hall effect sensor, a stress sensor, a strain sensor, a spring sensor, a piezo sensor, a distance sensor, a pneumatic pressure sensor, an opto-electronic measurement system marker, or a hydraulic pressure sensor.

11. The surgical system of claim 9, wherein the indicator further comprises a indicia associated with the first shaft.

12. The surgical system of claim 9, wherein the second shaft does not extend past the first shaft.

* * * * *